United States Patent
Schertl

(10) Patent No.: US 6,392,107 B2
(45) Date of Patent: May 21, 2002

(54) PROCESS FOR ISOMERIZING DICHLOROBUTENES

(75) Inventor: Peter Schertl, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/804,894

(22) Filed: Mar. 13, 2001

(30) Foreign Application Priority Data

Mar. 16, 2000 (DE) .......................................... 100 12 712

(51) Int. Cl.[7] .............................................. C07C 21/22
(52) U.S. Cl. ...................................................... 570/236
(58) Field of Search ......................................... 570/236

(56) References Cited

U.S. PATENT DOCUMENTS

| | | | | |
|---|---|---|---|---|
| 4,237,074 A | * | 12/1980 | Ito et al. ...................... | 570/236 |
| 4,895,993 A | * | 1/1990 | Mark et al. ................... | 570/236 |

* cited by examiner

*Primary Examiner*—Alan Siegel
(74) *Attorney, Agent, or Firm*—Joseph C. Gil; Noland J. Cheung

(57) ABSTRACT

This invention relates to a process for isomerizing 1,4-dichloro-2-butene to yield 3,4-dichloro-1-butene or 3,4-dichloro-1-butene to yield 1,4-dichloro-2-butene, characterized in that the catalyst used comprises a compound of the formula $CpFe(CO)_2X$, wherein Cp denotes a cyclopentadienyl derivative of the general formula (I),

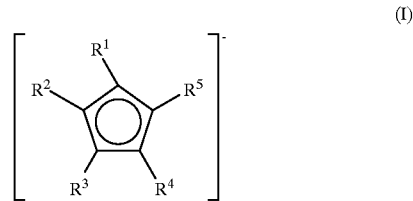

wherein $R^1$ to $R^5$ mutually independently denote H, $C_1$ to $C_{12}$ alkyl, $C_5$ to $C_8$ cycloalkyl, which may in turn bear $C_1$ to $C_{12}$ alkyl groups, $C_6$ to $C_{14}$ aryl, alkylaryl, arylalkyl, wherein two adjacent residues may together form saturated or unsaturated $C_3$ to $C_{14}$ cycles, or denote— $SiR^6R^7R^8$, wherein $R^6$ to $R^7$ may mutually independently mean $C_1$ to $C_4$ alkyl, $C_5$ to $C_8$ cycloalkyl or $C_6$ to $C_{14}$ aryl, and X denotes F, Cl, Br.

8 Claims, No Drawings

US 6,392,107 B2

PROCESS FOR ISOMERIZING DICHLOROBUTENES

FIELD OF THE INVENTION

This invention relates to a process for isomerizing 1,4-dichloro-2-butene to yield 3,4-dichloro-1-butene or 3,4-dichloro-1-butene to yield 1,4-dichloro-2-butene, characterized in that the catalyst used comprises a compound of the formula $CpFe(CO)_2X$.

3,4-Dichloro-1-butene is an important intermediate in the production of 2-chloroprene, which is used on a large industrial scale as a monomer in the production of polychloroprene rubber.

When butadiene is chlorinated, a mixture of cis-1,4-dichloro-2-butene, trans-1,4-dichloro-2-butene and 3,4-dichloro-1-butene is obtained which contains approx. 65% cis- and trans-1,4-dichloro-2-butene and approx. 35% 3,4-dichloro-1-butene. These isomers are usually present in the mixture in equilibrium, wherein the ratio is determined by production conditions. For simplicity's sake, cis- and trans-1,4-dichloro-2-butene are hereinafter referred to together as 1,4-dichloro-2-butene. This mixture may be separated by distillation on the basis of differing boiling points (1,4-dichloro-2-butene: 154-9° C. and 3,4-dichloro-1-butene: 123° C.). Since only 3,4-dichloro-1-butene is suitable for the production of 2-chloroprene, the 1,4-dichloro-2-butene must be isomerized to yield 3,4-dichloro-1-butene.

BACKGROUND OF THE INVENTION

Conventional processes for isomerizing 1,4-dichloro-2-butene to yield 3,4-dichloro-1-butene or vice versa are based upon the use of suitable isomerization catalysts, which ensure that equilibrium is rapidly established between the isomers in 1,4-dichloro2-butene or 3,4-dichloro1-butene at elevated temperatures. In most processes, metal salts of copper are used in the presence of further additives, which serve to achieve elevated reaction rates.

DE-A-2 138 790 discloses a process for isomerizing 1,4-dichloro-2-butene to yield 3,4-dichloro-1-butene or vice versa at 80 to 160° C. by means of copper naphthenate, dinitrile and amide. DE-A-2 143 157 describes an isomerization process in the presence of copper salts and oxime derivatives at 80 to 160° C. DE-A-2 200 780 claims a process which contains a mixture of a copper compound and an organic phosphorus compound as catalyst. DE-A-2 107 468 discloses the use of copper naphthenate and nitro compounds, while DE-A-2 130 488 discloses the use of copper naphthenate and nitroanilines. DE-A-2 212 235 describes an isomerization process by means of a copper compound and urea derivative. DE-A-2 206 971 claims the use of a mixture of copper compound and an aniline derivative containing chlorine. U.S. Pat. No. 4,895,993 describes an isomerization process in the presence of a catalyst consisting of a copper compound and a dithiocarbamate or trithiocarbamate derivative.

Rostovshchikova et al. describes in *Zh. Obschch. Khim.* 1994, 64, 12, the use of triphenylphosphine or in *Kinet. Katal.* 1992, 33, 314 the use of various dialkyl sulfides in the presence of copper halides for catalytic isomerization. In *Arm. Khim. Zh.* 1987, 40, 709, Asatryan. et al. describes the action of various isomerization catalysts based on halide salts of copper, iron or zinc in the presence of amine derivatives such as triethylamine, diethylamine, triethanolamine, ethylenediamine or aniline. Asatryan et al. investigated in *Arm. Khim. Zh.* 1988, 41, 278 the action of macrocyclic polyethers or polyethylene glycols and in *Arm. Khim. Zh.* 1988, 41, 273 the influence of benzonitrile, nitrobenzene, DMF, dimethyl sulfone or acetophenone.

A disadvantage of all these processes is that the transformation rates are comparatively low and a large quantity of unwanted secondary products is formed. Moreover, elevated concentrations of the particular catalysts are required in order to achieve economically necessary isomerization rates, which entails considerable effort in recovering the catalyst and gives rise to large quantities of waste containing heavy metals. The described systems are, furthermore, extremely corrosive and require special materials if it is to be possible to perform the isomerization on an industrial scale.

In *J. Organomet. Chem.* 1971, 29, 307–311, Henrici-Olivé and Olivé describe catalysts for isomerizing dichlorobutenes, among which cyclopentadienyliron dicarbonyl dimer, $[CpFe(CO)_2]_2$, wherein Cp denotes cyclopentadienyl, has proved to be a highly active catalyst, which may be used without the addition of activity-promoting additives. The disadvantage of the described catalyst is its elevated price, which does not justify use on an industrial scale.

SUMMARY OF THE INVENTION

The object of the present invention was accordingly to provide a catalyst system which first, ensures elevated transformation rates, catalyzes selectively, and with reduced formation of secondary products, may be used at low concentration and gives rise to less corrosion.

This object is achieved by the provision of a process for isomerizing 1,4-dichloro-2-butene to yield 3,4-dichloro-1-butene or 3,4-dichloro-1-butene to yield 1,4-dichloro-2-butene, characterized in that the catalyst comprises a compound of the formula $CpFe(CO)_2X$, wherein Cp denotes a cyclopentadienyl derivative of the general formula (I),

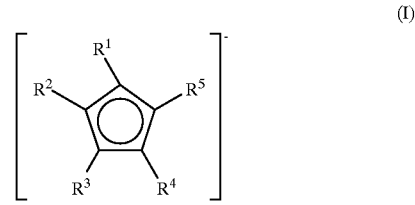

(I)

wherein $R^1$ to $R^5$ mutually independently denote H, $C_1$ to $C_{12}$ alkyl, $C_5$ to $C_8$ cycloalkyl, which may, in turn, bear $C_1$ to $C_{12}$ alkyl groups, $C_6$ to $C_{14}$ aryl, alkylaryl, arylalkyl, wherein two adjacent residues may together form saturated or unsaturated $C_3$ to $C_{14}$ cycles, or denote—$SiR^6R^7R^8$, wherein $R^6$ to $R^7$ may mutually independently mean $C_1$ to $C_4$ alkyl, $C_5$ to $C_8$ cycloalkyl or $C_6$ to $C_{14}$ aryl, and X denotes F, Cl, Br, I.

DETAILED DESCRIPTION OF THE INVENTION

The invention relates to a process for isomerizing 1,4-dichloro-2-butene to yield 3,4-dichloro-1-butene or 3,4-dichloro-1-butene to yield 1,4-dichloro-2-butene, characterized in that the catalyst comprises a compound of the formula $CpFe(CO)_2X$, wherein Cp denotes a cyclopentadienyl derivative of the general formula (I),

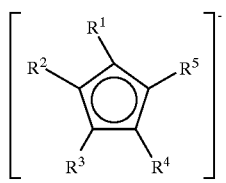

(I)

wherein $R^1$ to $R^5$ mutually independently denote H, $C_1$ to $C_{12}$ alkyl, $C_5$ to $C_8$ cycloalkyl, which may, in turn, bear $C_1$ to $C_{12}$ alkyl groups, $C_6$ to $C_{14}$ aryl, alkylaryl, arylalkyl, wherein two adjacent residues may together form saturated or unsaturated $C_3$ to $C_{14}$ cycles, or denote—$SiR^6R^7R^8$, wherein $R^6$ to $R^7$ may mutually independently mean $C_1$ to $C_4$ alkyl, $C_5$ to $C_8$ cycloalkyl or $C_6$ to $C_{14}$ aryl, and X denotes F, Cl, Br, I.

$C_1$–$C_{12}$ alkyl are taken to mean all linear or branched, saturated or unsaturated alkyl residues having 1 to 12 C atoms known to the person skilled in the art, such as methyl, ethyl, n-propyl, i-propyl, n-butyl, i-butyl, t-butyl, n-pentyl, i-pentyl, neopentyl, n-hexyl, i-hexyl, heptyl, octyl, nonyl, decyl, undecyl and dodecyl, together with the unsaturated homologues thereof.

$C_5$ to $C_8$ cycloalkyl are taken to mean all cyclic alkyl residues having 5 to 8 C atoms known to the person skilled in the art, such as cyclopentyl, cyclohexyl, cycloheptyl, cyclooctyl, together with the unsaturated homologues thereof.

$C_6$ to $C_{14}$ aryl are taken to mean all aryl residues having 6 to 14 C atoms known to the person skilled in the art, such as phenyl, naphthenyl, fluorenyl, anthracenyl and phenanthranyl.

Preferred cyclopentadiene derivatives are cyclopentadienyl, methylcyclo-pentadienyl, indenyl, tetrahydroindenyl and fluorenyl. The process is advantageously performed by a) adding the iron complex according to the present invention to 1,4-dichloro-2-butene or 3,4-dichloro-1-butene at a temperature in the range from 40 to 200° C., preferably in the range from 100 to 150° C.,
b) allowing the catalyst to act for between 1 and 180 minutes, preferably between 15 and 45 minutes, in order to establish an equilibrium,
c) continuously removing a mixture of 1,4-dichloro-2-butene and 3,4-dichloro-1-butene and then separating it by distillation,
d) introducing the unwanted component from the distillation performed in c) into the reaction system and optionally
e) simultaneously with c), continuously supplying 1,4-dichloro-2-butene and/or 3,4-dichloro-1-butene to the reaction system.

Additionally, two or more different iron complexes according to the present invention may also be used in the form of a mixture.

The process may proceed either discontinuously or continuously at between 0.01 bar and 10 bar, preferably between 0.1 and 1.0 bar, wherein it is advisable initially, to produce a relatively highly concentrated solution of the catalyst system, preferably $10^{-1}$ to 1 mol of Fe/L, in 1,4-dichloro-2-butene or 3,4-dichloro-1-butene and to add continuously thereto, respectively, a relatively large quantity of 1,4-dichloro-2-butene or 3,4-dichloro-1-butene, such that the desired concentration of the catalyst is obtained, wherein respectively 1,4-dichloro-2-butene or 3,4-dichloro-1-butene is continuously supplied, a mixture of 1,4-dichloro-2-butene and 3,4-dichloro-1-butene is continuously removed and then separated by distillation.

The following practical Examples illustrate the invention in greater detail, but without restricting the invention to the Examples.

EXAMPLES

Example 1

240.0 g of 1,4-dichloro-2-butene are introduced into a 500 mL round-bottomed flask equipped with an internal thermometer, reflux a condenser and pressure relief valve, 60.8 mg (0.2 mmol) of dicarbonylcyclopentadienyliron iodide are added at 100° C. and the mixture is stirred for 3 h at this temperature.

Over the period of the reaction, samples are taken at specified intervals and tested by gas chromatography for the content thereof of 3,4-dichloro-1-butene, cis-1,4-dichloro-2-butene, trans-1,4-dichloro-2-butene and any possibly formed secondary products, such as 1-chloroprene. The starting point of the reaction is defined by the addition of dicarbonyl cyclopentadienyliron iodide. Samples, each of a volume of approx. 2 ml, are taken at the starting point, after 2, 5, 15, 30, 90 and 180 minutes.

Example 2

240.0 g of 1,4-dichloro-2-butene are initially introduced into the test setup described in Example 1, 60.8 mg (0.2 mmol) of dicarbonylcyclopentadienyliron iodide are added at 140° C. and the mixture is stirred for 3 h at this temperature. The timing and nature of sampling and testing of the samples proceed as stated in greater detail in Example 1.

Example 3 (Comparative Example)

240.0 g of 1,4-dichloro-2-butene are initially introduced into the test setup described in Example 1, 70.8 mg (0.2 mmol) of cyclopentadienyliron dicarbonyl dimer are added at 140° C. and the mixture is stirred for 3 h at this temperature. The timing and nature of sampling and testing of the samples proceed as stated in greater detail in Example 1.

Example 4 (Comparative Example)

240.0 g of 1,4-dichloro-2-butene are initially introduced into the test setup described in Example 1, 141.6 mg (0.4 mmol) of cyclopentadienyliron dicarbonyl dimer are added at 140° C. and the mixture is stirred for 3 h at this temperature. The timing and nature of sampling and testing of the samples proceed as stated in greater detail in Example 1.

Example 5 (Comparative Example)

232.0 g of 1,4-dichloro-2-butene are initially introduced under nitrogen into a 500 mL round-bottomed flask equipped with an internal thermometer, reflux condenser and pressure relief valve, 9.5 g (94 mmol) of triethylamine are added at 50° C. and the mixture is stirred for 4 h at this temperature. 10.3 g (104 mmol) of copper(I) chloride are then added at 50° C. and the mixture is stirred for a further 8 h at this temperature.

240.0 g of 1,4-dichloro-2-butene are initially introduced into the test setup described in Example 1, 84 g of the catalyst solution (produced as described above) are added at 130° C., such that a mixture temperature of 105° C. is established, and the mixture is stirred for 3 h at this temperature. The nature of sampling and testing of the samples proceed as stated in greater detail in Example 1. Samples are taken at the starting point of the reaction, i.e. immediately after addition of the catalyst solution, and after 5, 30, 90, 180 and 360 minutes.

Example 6 (Comparative Example)

240.0 g of 1,4-dichloro-2-butene are initially introduced into the test setup described in Example 1, 84 g of the catalyst solution (produced as described in Example 21) are added at 160° C., such that a mixture temperature of 130° C. is established, and the mixture is stirred for 3 h at this temperature. The nature of sampling and testing of the samples proceed as stated in greater detail in Example 1. Samples are taken at the starting point of the reaction, i.e. immediately after addition of the catalyst solution, and after 5, 30, 90, 180 and 360 minutes.

The Examples according to the present invention demonstrate that the conventional copper (I) chloride/triethylamine system gives rise to the formation of distinctly larger quantities of secondary products, that an elevated catalyst concentration is required in order to achieve adequate transformation rates and that isomerization efficiency is lower.

Under comparable reaction conditions, using cyclopentadienyliron dicarbonyl dimer gives rise to lower conversion rates, relative to the introduced quantity of iron.

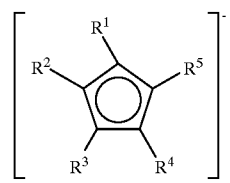

wherein
R$^1$ to R$^5$ mutually independently denote H, C$_1$ to C$_{12}$ alkyl, C$_5$ to C$_8$ cycloalkyl, which may, in turn, bear C$_1$ to C$_{12}$ alkyl groups, C$_6$ to C$_{14}$ aryl, alkylaryl, arylalkyl, wherein two adjacent residues may together form saturated or unsaturated C$_3$ to C$_{14}$ cycles, or denote—SiR$^6$R$^7$R$^8$, wherein R$^6$ to R$^7$ may mutually independently mean C$_1$ to C$_4$ alkyl, C$_5$ to C$_8$ cycloalkyl or C$_6$ to C$_{14}$ aryl, and X denotes F, Cl, Br, I.

2. A process according to claim 1, wherein isomerization is performed at a temperature in the range from 40 to 200° C.

3. A process according to claim 2, wherein the cyclopentadienyl derivative is selected from the group consisting of cyclopentadienyl, methylcyclopentadienyl, indenyl or a mixture of 2 or 3 of these compounds.

4. A process according to claim 1, wherein
a) said catalyst is added to 1,4-dichloro-2-butene at a temperature in the range from 40 to 180° C.,
b) said catalyst is allowed to act for between 1 and 180 minutes in order to establish an equilibrium,

TABLE 1

| | | | | | | Content [%] | | | | | |
|---|---|---|---|---|---|---|---|---|---|---|---|
| | | Concentration | | Concentration | Temperature | 3,4-dichloro-1-butene | | | | | 1-chloroprene |
| Example | Complex$^{a)}$ | [mmol/L] | Additive | [mmol/L] | [° C.] | 0 min | 5 min | 15 min | 30 min | 90 min | 180 min | 180 min |
| 1 | CpFe(CO)$_2$I | 1.0 | — | — | 100 | 2.34 | 14.10 | 16.98 | 18.82 | 19.82 | 19.91 | 0.03 |
| 2 | CpFe(CO)$_2$I | 1.0 | — | — | 140 | 2.75 | 18.78 | 20.90 | 21.73 | 22.22 | 21.98 | 0.01 |
| 3 | [CpFe(CO)$_2$]$_2$ | 1.0 | — | — | 140 | 2.47 | 9.19 | 19.27 | 22.88 | 22.89 | 23.08 | 0.04 |
| 4 | [CpFe(CO)$_2$]$_2$ | 2.0 | — | — | 140 | 2.58 | 10.75 | 19.46 | 23.23 | 23.24 | 23.18 | 0.05 |
| 5 | CuCl | 128 | Et$_3$N | 115 | 105 | 8.96 | 13.23 | — | 16.94 | 17.21 | 17.25 | 0.93 |
| 6 | CuCl | 128 | Et$_3$N | 115 | 130 | 9.54 | 15.47 | — | 18.13 | 17.82 | 18.41 | 2.73 |

$^{a)}$CpFe(CO)$_2$I = dicarbonylcyclopentadienyliron iodide, [CpFe(CO)$_2$]$_2$ = cyclopentadienyliron dicarbonyl dimer Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing 3,4-dichloro-1-butene comprising the step of isomerizing 1,4-dichloro-2-butene in the presence of a catalyst compound of the formula CpFe(CO)$_2$X, wherein Cp denotes a cyclopentadienyl derivative of the general formula (I), c) a mixture of 1,4-dichloro-2-butene and 3,4-dichloro-1-butene is continuously removed and is then separated by distillation, d) the unwanted component from the distillation performed in c) is introduced into the reaction system and optionally e) simultaneously with c), 1,4-dichloro-2-butene and/or 3,4-dichloro-1-butene are continuously supplied to the reaction system.

5. A process for producing 1,4-dichloro-2-butene comprising the step of isomerizing 3,4-dichloro-1-butene to yield 1,4-dichloro-2-butene, in the presence of a catalyst compound of the formula CpFe(CO)$_2$X, wherein Cp denotes a cyclopentadienyl derivative of the general formula (I),

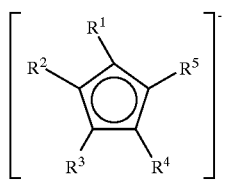 (I)

wherein
$R^1$ to $R^5$ mutually independently denote H, $C_1$ to $C_{12}$ alkyl, $C_5$ to $C_8$ cycloalkyl, which may in turn bear $C_1$ to $C_{12}$ alkyl groups, $C_6$ to $C_{14}$ aryl, alkylaryl, arylalkyl, wherein two adjacent residues may together form saturated or unsaturated $C_3$ to $C_{14}$ cycles, or denote—$SiR^6R^7R^8$, wherein $R^6$ to $R^7$ may mutually independently mean $C_1$ to $C_4$ alkyl, $C_5$ to $C_8$ cycloalkyl or $C_6$ to $C_{14}$ aryl, and X denotes F, Cl, Br, I.

6. A process according to claim 5, wherein said isomerization is performed at a temperature in the range from 40 to 200° C.

7. A process according to claim 6, wherein the cyclopentadienyl derivative is selected from the group consisting of cyclopentadienyl, methylcyclopentadienyl, indenyl or a mixture of 2 or 3 of these compounds.

8. A process according to claim 1, wherein
a) the catalyst compound added to 3,4-dichloro-1-butene at a temperature in the range from 40 to 180° C.,
b) the catalyst compound is allowed to act for between 1 and 180 minutes in order to establish an equilibrium,
c) a mixture of 1,4-dichloro-2-butene and 3,4-dichloro-1-butene is continuously removed and is then separated by distillation,
d) the unwanted component from the distillation performed in c) is introduced into the reaction system and optionally
e) simultaneously with c), 1,4-dichloro-2-butene and/or 3,4-dichloro-1-butene are continuously supplied to the reaction system.

* * * * *